(12) United States Patent
Moldt et al.

(10) Patent No.: US 6,180,649 B1
(45) Date of Patent: Jan. 30, 2001

(54) 1-(4-PIPERIDYL)-BENZIMIDAZOLES HAVING NEUROTROPHIC ACTIVITY

(75) Inventors: Peter Moldt, Humlebaek; Bjarne Hugo Dahl, Allerod; Jorgen Drejer, Vaerlose, all of (DK); Oskar Axelsson, Malmö (SE)

(73) Assignee: NeroSearch A/S, Glostrup (DK)

(*) Notice: Under 35 U.S.C. 154(b), the term of this patent shall be extended for 0 days.

(21) Appl. No.: 09/171,530

(22) PCT Filed: Apr. 21, 1997

(86) PCT No.: PCT/EP97/02011
§ 371 Date: Nov. 19, 1998
§ 102(e) Date: Nov. 19, 1998

(87) PCT Pub. No.: WO97/40035
PCT Pub. Date: Oct. 30, 1997

(30) Foreign Application Priority Data

Apr. 19, 1996 (DK) .................................................. 0459/96

(51) Int. Cl.[7] ........................ A61K 31/445; C07D 401/04
(52) U.S. Cl. ........................................... 514/322; 546/199
(58) Field of Search ............................ 514/322; 546/199

(56) References Cited

U.S. PATENT DOCUMENTS

| | | | |
|---|---|---|---|
| 3,196,157 | 7/1965 | Janssen et al. | 546/199 |
| 3,318,900 | 5/1967 | Janssen | 514/322 |
| 3,963,727 | 6/1976 | Ueno et al. | 514/322 |
| 3,989,707 | 11/1976 | Janssen et al. | 546/199 |
| 4,031,226 * | 6/1977 | Soudijn et al. | 514/278 |
| 4,264,613 | 4/1981 | Regnier et al. | 514/322 |

FOREIGN PATENT DOCUMENTS

| | | |
|---|---|---|
| 197877 | 8/1965 | (BE) . |
| 2636614 | 2/1977 | (DE) . |
| 178081 | 7/1979 | (DK) . |
| 141751 | 6/1980 | (DK) . |
| 0092391 | 10/1983 | (EP) . |
| 0636614 | 2/1995 | (EP) . |
| 9522327 | 8/1995 | (WO) . |

OTHER PUBLICATIONS

Chemical Abstracts, vol. 86, (1977), Abstract No. 86:72634h.
Chemical Abstracts, vol. 86, (1977), Abstract No. 86:189929z.
Chemical Abstracts, vol. 86, (1977), Abstract No. 86:189933w.
Chemical Abstracts, vol. 87, (1977), Abstract No. 87:53289d.
Obase, Hiroyuki et al., J. Heterocyclic Chem., vol. 20, (1983), pp. 565–573.
Henning, Rainer et al., J. Med. Chem., vol. 30, (1987), pp. 814–819.
J. Chlan–Fourney et al., Society for Neuroscience, vol. 23, p. 1932 (1997).
Groenborg M. et al., Neuroprotection by a Novel Compound, NS521, J. Pharm. Exp. Ther., vol. 290, No. 1 (1999).
Chem. Pharm. Bull., vol. 30, No. 2, Feb. 1982 pp. 462–473.
Helvetica Chimica Acta, vol. 43, No. 5, Aug. 1, 1960 pp. 1298–1313.
Pharmazie vol. 30, No. 11, Nov. 1975 pp. 728–730.
Costall et al. "Dopamine antagonistic effects . . . " CA 91:168329, 1978.*
Chlan–Fourney "Induction of brain derived . . . " Biosis No. 199799831259, 1997.*

* cited by examiner

*Primary Examiner*—Ceila Chang
(74) *Attorney, Agent, or Firm*—Birch, Stewart, Kolasch & Birch, LLP

(57) ABSTRACT

The present invention discloses compounds of the formula

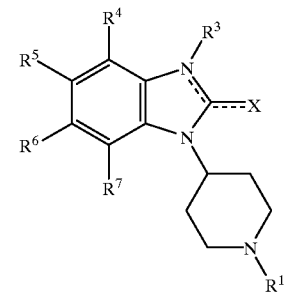

wherein the dotted bonds are optional extra bonds allowing any tautomeric isomers compatible with substituents X and $R^3$;

Figure 1:
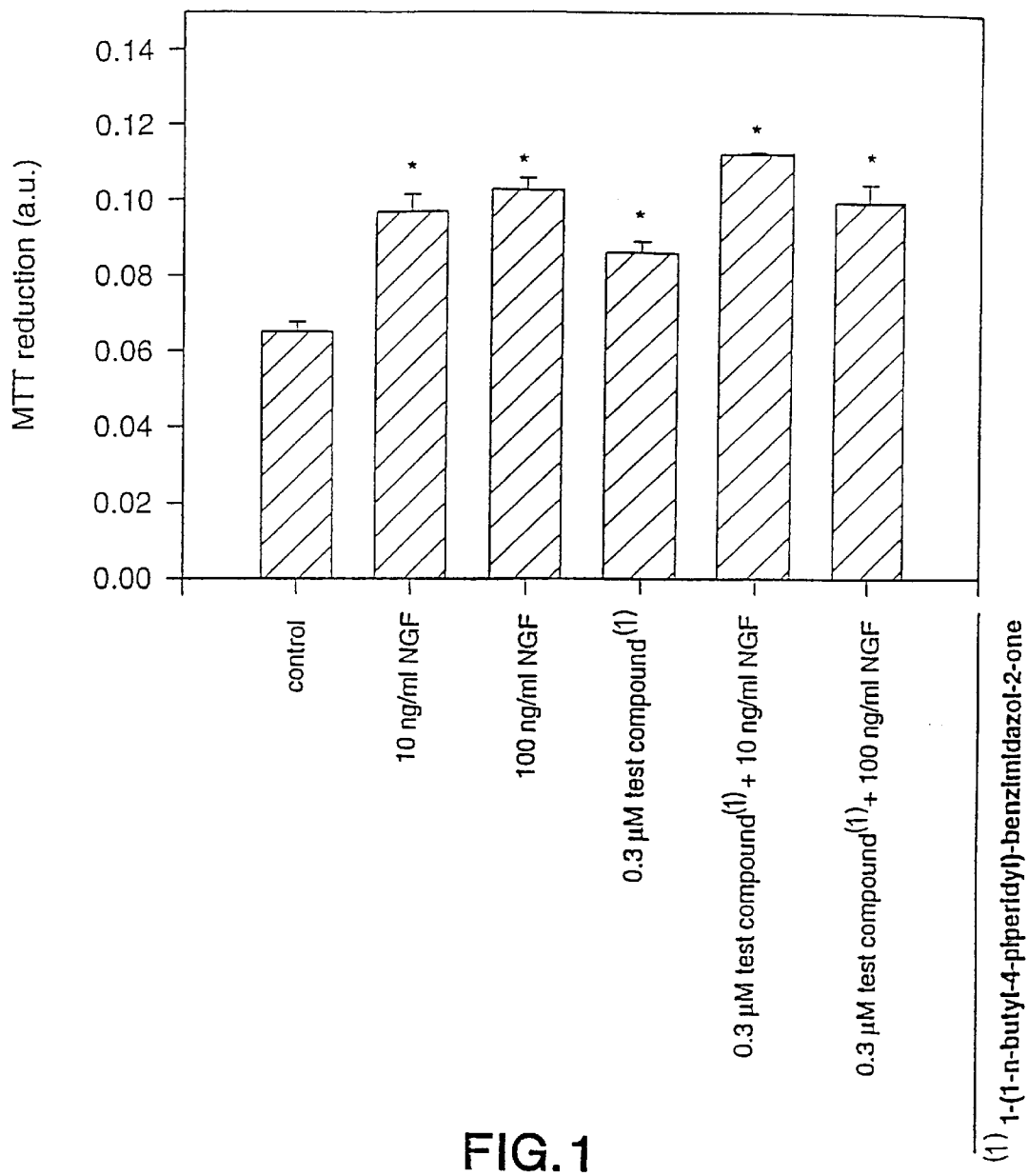

$R^3$ is non-existing, hydrogen, or alkyl;

X is O, S, imino, alkoxy, alkylthio, or amino;

$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro;

CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3; —$(CH_2)_p$—O-acyl wherein p is 0, 1,2, or 3;

or a pharmaceutically acceptable addition salt thereof. The compounds are useful as pharmaceuticals, for example, in the treatment of traumatic lesions of peripheral nerves, the medulla, and/or the spinal cord, cerebral ischaemic neuronal damage, neuropathy and especially peripheral neuropathy, dementia, Alzheimer's disease, Huntington's disease, Parkinson's disease, amyotrophic lateral sclerosis, or any other neurodegenerative disease.

10 Claims, 3 Drawing Sheets

1-(4-PIPERIDYL)-BENZIMIDAZOLES HAVING NEUROTROPHIC ACTIVITY

This application is the national phase under 35 U.S.C. §371 of prior PCT International Application No. PCT/EP97/02011 which has an International filing date of Apr. 21, 1997 which designated the United States of America, the entire contents of which are hereby incorporated by reference.

The present invention relates to certain neurotrophically active 1-(4-piperidyl)-benzimidazoles and their use in the treatment of neurodegenerative diseases and for the regeneration or prevention of degeneration of lesioned and damaged neurons.

BACKGROUND OF THE INVENTION

Growth (or neurotrophic) factors promote the differentiation, growth and survival of numerous peripheral and central nervous system neurons during development and adulthood. The molecular characteristics, regulation and signal transduction mechanism for a number of neurotrophic factors have been identified. The most therapeutically promising of these molecules are nerve growth factor (NGF), brain-derived neurotrophic factor (BNDF), ciliary neurotrophic factor (CNTF), basic fibroblast growth factor (bFGF), insulin-like growth factor-I (IGF-I), and glial cell-line derived neurotrophic factor (GDNF).

Available data suggests that neurotrophic factors will be useful in the treatment of neurodegenerative diseases such as Alzheimer's disease, Parkinson's disease and amyotrophic lateral sclerosis. Additionally neurotrophic factors have shown beneficial effects in animal models of peripheral nerve damage and toxin induced neuropathies (CNS Drugs, 2(6), 465–478 (1994)).

Various rat studies predict that compounds mimicking or enhancing the function of NGF can rescue septal colinergic neurons and alleviate benign forgetfulness and the memory impairment seen in senile dementia ( Science, Vol. 264, 772–774 (1994)).

Recent studies have shown that NGF has a neuroprotective effect on hippocampal neurons after cerebral ischaemia, which predicts a potential therapeutic role for NGF in the treatment of cerebral ischaemic neuronal damage (NeuroReport, vol. 6, No 4, 669–672 (1995)).

Growth factors initiate their biological action by binding to specific cell surface receptors. Binding of the growth factor to its receptor activates the intracellular signal transduction, leading to the generation of various second messengers and activation of enzyme cascades, involving tyrosine kinases and protein kinase C, and culminates in a biological effect. The intracellular signal transduction pathway is not yet fully understood.

NGF and related neurotrophins are large peptides, which makes them unlikely therapeutic candidates. Poor pharmacokinetic parameters (e.g. poor oral absorption and short in vivo half life), and administration to the target organs represent the major problems.

The identification of compounds with physicochemical properties different from the neurotrophins but capable of interaction with the neurotrophin-receptors is considered to be extremely important for the development of effective treatments of diseases and disorders responsive to neurotrophic factors.

The inventors of the present invention have found that the 1-(4-piperidyl)-benzimidazoles of formula (I) possess valuable neurotrophic activity. The neurotrophic activity found by the inventors of the present invention has not been ascribed to a specific step in the interaction between NGF and its receptor or in the NGF signal transduction pathway.

The neurotrophic activity of the compounds of formula (I), make them useful in the treatment of various nerve degenerative diseases, such as for example Alzheimer's disease, Parkinson's disease, Huntington's disease, and amyotrophic lateral sclerosis, and in alleviating benign forgetfulness and the memory impairment seen in senile dementia or in connection with neurodegenerative diseases. Furthermore, the compounds are indicated to be useful in the treatment of neuropathy and especially peripheral neuropathy caused by e.g. genetic abnormalities and other conditions such as diabetes, polio, herpes and AIDS, and most especially neuropathy and peripheral neuropathy experienced by most cancer patients after or during chemotherapy.

The compounds of formula (I) are considered to be particularly useful in the treatment of traumatic lesions of peripheral nerves, the medulla, and/or the spinal cord, and in the treatment of cerebral ischaemia, e.g. ischaemic neuronal damage following cardiac arrest, stroke, or postasphyxial brain damage in newborns, or following near-drowning.

OBJECTS OF THE INVENTION

It is an object of the present invention to provide a method for the treatment of disorders or diseases responsive to the activity of neurotrophic agents, such as traumatic lesions of peripheral nerves, the medulla, and/or the spinal cord, cerebral ischaemic neuronal damage, neuropathy and especially peripheral neuropathy, Alzheimer's disease, Huntington's disease, Parkinson's disease, amyotrophic lateral sclerosis or any other neurodegenerative disease, and memory impairment connected to dementia. Another object of the present invention is to provide a method for the prevention of the degenerative changes connected with the above diseases and disorders.

Still another object of the present invention is to provide novel 1-(4-piperidyl)-benzimidazoles, and novel pharmaceutical compositions containing these compounds which will be useful in the treatment of or prevention of the ailments mentioned above.

SUMMARY OF THE INVENTION

The invention then, inter alia, comprises the following, alone or in combination:

A method of treating a disorder or disease of a living animal body, including a human, which is responsive to the activity of a neurotrophic agent, which comprises administering to such a living animal body, including a human, in need thereof a therapeutically effective amount of a compound selected from those having the formula:

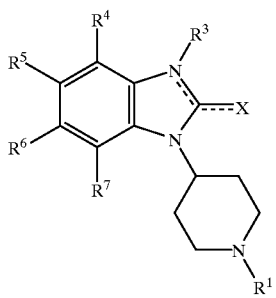

(I)

wherein
the dotted bonds are optional extra bonds allowing any tautomeric isomers compatible with substituents X and $R^3$;
$R^3$ is non-existing, hydrogen, or alkyl;
X is O, S, imino, alkoxy, alkylthio, or amino;
$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and
$R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3; —$(CH_2)_p$—O-acyl wherein p is 0, 1,2, or 3; or a pharmaceutically acceptable addition salt thereof;

a method of treating a disorder or disease of a living animal body, including a human, which is responsive to the activation or potentiation of nerve growth factor(s), which comprises administering to such a living animal body, including a human, in need thereof a therapeutically-effective amount of a compound selected from those having the formula:

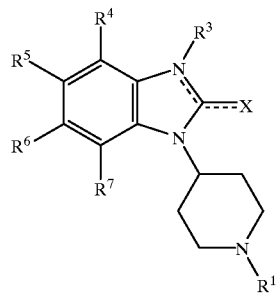

wherein
the dotted bonds are optional extra bonds allowing any tautomeric isomers compatible with substituents X and $R^3$;
$R^3$ is non-existing, hydrogen, or alkyl;
X is O, S, imino, alkoxy, alkylthio, or amino;
$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and
$R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3; —$(CH_2)_p$—O-acyl wherein p is 0, 1,2, or 3; or a pharmaceutically acceptable addition salt thereof;

a method of treating traumatic lesions of peripheral nerves, the medulla, and/or the spinal cord, cerebral ischaemic neuronal damage, neuropathy and especially peripheral neuropathy, dementia, Alzheimer's disease, Parkinson's disease, Huntington's disease, amyotrophic lateral sclerosis, or any other neurodegenerative disease, of a living animal body, including a human, which comprises administering to such a living animal body, including a human, in need thereof a therapeutically effective amount of a compound selected from those having the formula:

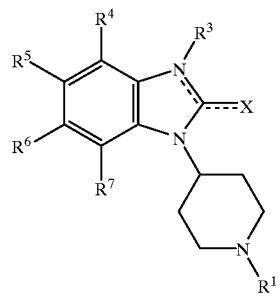

wherein
the dotted bonds are optional extra bonds allowing any tautomeric isomers compatible with substituents X and $R^3$;
$R^3$ is non-existing, hydrogen, or alkyl;
X is O, S, imino, alkoxy, alkylthio, or amino;
$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and
$R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3;—$(CH_2)_p$—O-acyl wherein p is 0, 1,2, or 3; or a pharmaceutically acceptable addition salt thereof;

a method of preventing the degenerative changes connected with cerebral ischaemic neuronal damage, neuropathy and especially peripheral neuropathy, Alzheimer's disease, Huntington's disease, Parkinson's disease, amyotrophic lateral sclerosis or any other neurodegenerative disease, of a living animal body, including a human, which comprises administering to such a living animal body, including a human, in need thereof a therapeutically effective amount of a compound selected from those having the formula:

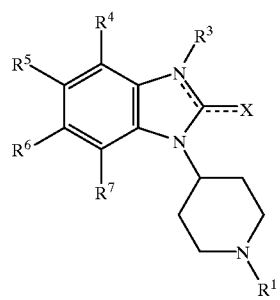

wherein
the dotted bonds are optional extra bonds allowing any tautomeric isomers compatible with substituents X and $R^3$;
$R^3$ is non-existing, hydrogen, or alkyl;
X is O, S, imino, alkoxy, alkylthio, or amino;

$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3;— $(CH_2)_p$—O-acyl wherein p is 0, ,2, or 3; or a pharmaceutically acceptable addition salt thereof;

a method as any above, wherein the compound employed is 1-(1-n-butyl-4-piperidyl)-benzimidazol-2-one, or 1-(1-benzyl-4-piperidyl)-5-fluoro-2-aminobenzimidazole, or a pharmaceutically acceptable addition salt thereof;

a method as any above, wherein the active ingredient is administered in form of a pharmaceutical composition thereof, in which it is present together with a pharmaceutically acceptable carrier of diluent;

the use of a compound having the formula

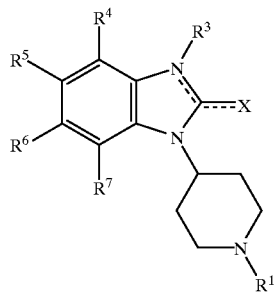

(I)

or a phaarmaceutically acceptable addition salt thereof wherein the dotted bonds are optional extra bonds allowing any tautomeric isomers compatible with substituents X and $R^3$;

$R^3$ is non-existing, hydrogen, or alkyl;

X is O, S, imino, alkoxy, alkylthio, or amino;

$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3; —$(CH_2)_p$—O-acyl wherein p is 0, 1,2, or 3, for the manufacture of a medicament for the treatment of a disorder or disease of a living animal body, including a human, which disorder or disease is responsive to the activity of a neurotrophic agent;

the use of a compound having the formula

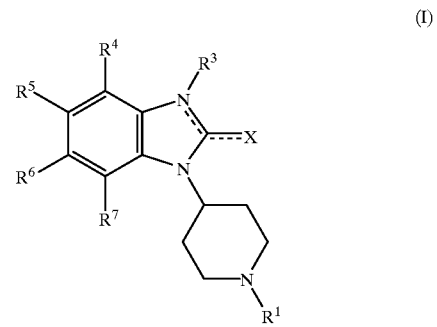

(I)

or a pharmaceutically acceptable addition salt thereof
wherein
the dotted bonds are optional extra bonds allowing any tautomeric isomers compatible with substituents X and $R^3$;
$R^3$ is non-existing, hydrogen, or alkyl;
X is O, S, imino, alkoxy, alkylthio, or amino;
$R^1$ is hydrogen, alky, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$—OH wherein n is 0, 1, 2, or 3; —$(CH_2)_m$—O-alkyl wherein m is 0, 1,2, or 3; —$(CH_2)_p$—O-acyl wherein p is 0, 1,2, or 3, for the manufacture of a medicament for the treatment of a disorder or disease of a living animal body, including a human, which disorder or disease is responsive to the activation or potentiation of nerve growth factor(s);

the use of a compound having the formula

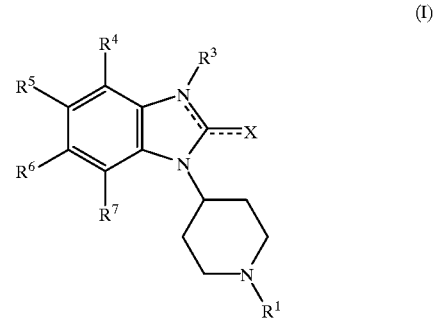

(I)

or a pharmaceutically acceptable addition salt thereof
wherein
the dotted bonds are optional extra bonds allowing any tautomeric isomers compatible with substituents X and $R^3$;
$R^3$ is non-existing, hydrogen, or alkyl;
X is O, S, imino, alkoxy, alkylthio, or amino;
$R^3$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$,—OH wherein n is 0,1, 2, or 3; —$(CH_2)_m$—O-alkyl wherein m is 0, 1,2, or 3; —$(CH_2)_p$—O-acyl wherein p is 0, 1,2, or 3, for the manufacture of a medicament for the treatment of traumatic lesions of peripheral nerves, the medulla, and/or the spinal cord, cerebral ischaemic neuronal damage, neuropathy and especially peripheral neuropathy, dementia, Alzheimer's disease, Huntingtons disease, Parkinson's disease, amyotrophic lateral sclerosis, or any other neurodegenerative disease, of a living animal body, including a human;

the use of a compound having the formula

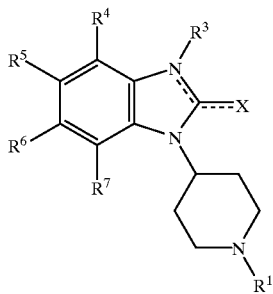

(I)

or a pharmaceutically acceptable addition salt thereof wherein the dotted bonds are optional extra bonds allowing any tautomeric isomers compatible with substituents X and $R^3$;

$R^3$ is non-existing, hydrogen, or alkyl;

X is O, S, imino, alkoxy, alkylthio, or amino;

$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$,—OH wherein n is 0, 1, 2, or 3; —$(CH_2)_m$—O-alkyl wherein m is 0, 1,2, or 3; —$(CH_2)_p$—O-acyl wherein p is 0, 1,2, or 3, for the manufacture of a medicament for the prevention of the degenerative changes connected with cerebral ischaemic neuronal damage, neuropathy and especially peripheral neuropathy, or Alzheimer's disease, Parkinson's disease, Huntington's disease, amyotrophic lateral sclerosis, or any other neurodegenerative disease, of a living animal body, including a human;

the use as any above, wherein the compound employed is 1-(1-n-butyl-4-piperidyl)-benzimidazol-2-one, or 1-(1-benzyl-4-piperidyl)-5-fluoro-2-aminobenzimidazole, or a pharmaceutically acceptable addition salt thereof;

a compound having the formula

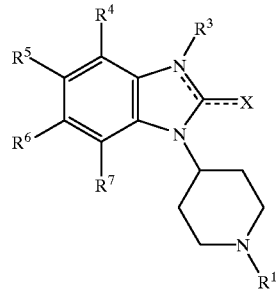

(II)

wherein the dotted bonds are optional extra bonds allowing any tautomeric isomers compatible with substituents X and $R^3$;

$R^3$ is non-existing, hydrogen, or alkyl;

X is O, S, imino, alkoxy, alkylthio, or amino;

$R^1$ is hydrogen, alkyl, alkenyl, alkynyl, cycloalkyl, cycloalkylalkyl, acyl, acylalkyl, alkoxyalkyl, dialkoxyalkyl, or phenylalkyl which may be substituted with alkyl, halogen, amino, nitro or cyano; and $R^4$, $R^5$, $R^6$ and $R^7$ independently of each other are hydrogen; halogen; amino; nitro; CN; $CF_3$; COOH; COO-alkyl; alkyl; acyl; alkoxy; —$(CH_2)_n$,—OH wherein n is 0, 1, 2, or 3; —$(CH_2)_m$—O-alkyl wherein m is 0, 1,2, or 3; —$(CH_2)_p$—O-acyl wherein p is 0, 1,2, or 3; or a pharmaceutically acceptable addition salt thereof; and a compound as any above which is 1-(1-n-butyl-4-piperidyl)-benzimidazol-2-one, or 1-(1-benzyl-4-piperidyl)-5-fluoro-2-aminobenzimidazole, or a pharmaceutically acceptable addition salt thereof;

a pharmaceutical composition comprising an effective amount of a compound as any above or a pharmaceutically acceptable addition salt thereof, together with at least one pharmaceutically acceptable carrier or diluent.

A preferred value of $R^1$ is alkyl.

Halogen is fluorine, chlorine, bromine, or iodine; chlorine, bromine and iodine are preferred.

Alkyl means straight chain alkyl, or branched chain alkyl of one to ten carbon atoms, inclusive of, but not limited to, methyl, ethyl, propyl, isopropyl, butyl, isobutyl, t-butyl, pentyl, hexyl; methyl, ethyl, propyl and isopropyl are preferred groups.

Alkenyl means a group of two to ten carbon atoms, containing one double bond, for example, but not limited to ethenyl, 1,2- or 2,3-propenyl, 1,2-, 2,3-, or 3,4-butenyl.

Alkynyl means a group of two to ten carbon atoms, containing one triple bond, for example, but not limited to ethynyl, 2,3-propynyl, 2,3- or 3,4-butynyl.

Cyclic alkyl means cycloalkyl of three to seven carbon atoms, inclusive of cyclopropyl, cyclobutyl, cyclopentyl, cyclohexyl and cycloheptyl.

Cycloalkylalkyl means cycloalkyl as above and alkyl as above, meaning for example, cyclopropylmethyl.

Alkoxy is O-alkyl, wherein alkyl is as defined above.

Alkylthio is S-alkyl, wherein alkyl is as defined above.

Phenylalkyl means phenyl, and alkyl as above.

Acyl is CHO or CO-phenyl or CO-alkyl wherein alkyl is as defined above.

Acylalkyl is CHO-alkyl, Phenyl-CO-alkyl, and alkyl-CO-alkyl wherein alkyl is as defined above.

Amino is $NH_2$ or NH-alkyl or N-(alkyl)$_2$, wherein alkyl is as defined above.

Imino is =NH or =N-alkyl, wherein alkyl is as defined above.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, benzoate, ascorbate, cinnamate, benzenesulfonate, methanesulfonate, stearate, succinate, glutamate, salicylate and the acetate. Such salts are formed by procedures well known in the art.

Further, the compounds of this invention may exist in unsolvated as well as in solvated forms with phaarmaceutically acceptable solvents such as water, ethanol and the like. In general, the solvated forms are considered equivalent to the unsolvated forms for the purposes of this invention.

Some of the compounds comprised by the scope of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l-(tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to one skilled in the art. Such methods include those discussed by J. Jaques, A. Collet, and S. Wilen in "Enantiomers, Racemates, and Resolutions", John Wiley and Sons, New York (1981).

The compounds of the invention can be prepared by, or analogous to, conventional procedures (see for example EP patent applications No. 477.819 and 604.353).

The compounds of the invention can thus be prepared as illustrated in the following reaction schemes:

a)

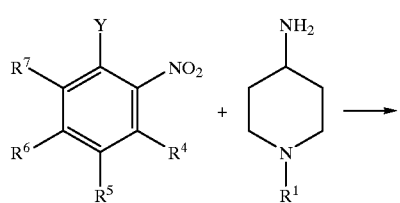

-continued

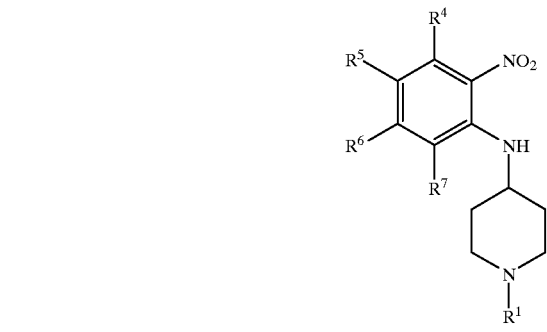

b)

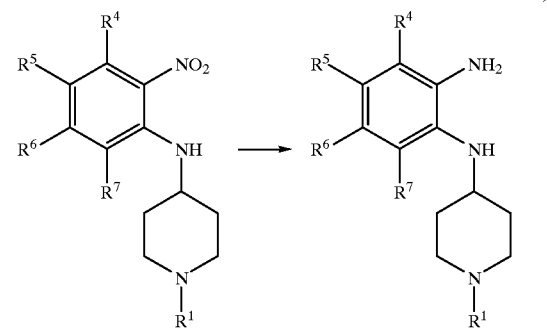

c)

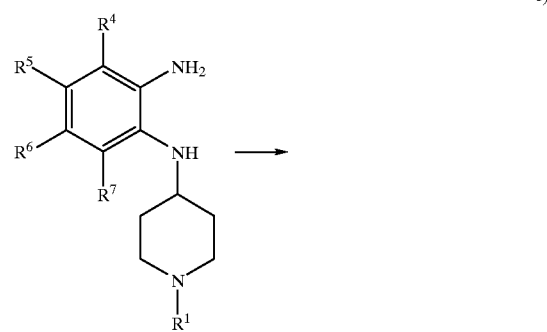

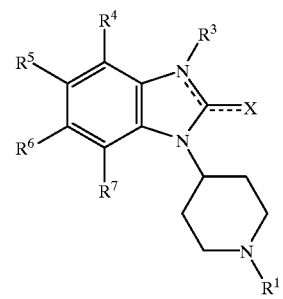

In the compounds in the reaction schemes a)-c) above, the substituents $R^1$, $R^3$, $R^4$, $R^5$, $R^6$, and $R^7$ have the meanings set forth above, and Y means halogen, preferentially fluoro.

The reaction in scheme a) is carried out using conventional procedures. Preferentially the reaction is carried out in an organic solvent, such as tetrahydrofuran, or N,N-dimethylformamide, in the presence of an organic or inorganic base (e.g. triethylamine, pyridine, sodium hydride, or potassium carbonate).

The reduction in scheme b) is carried out using common procedures for reducing nitro substituents. The reduction is preferentially carried out in an organic solvent, such as ethanol or tetrahydrofuran, using Pd/C or Raney Nickel as a catalyst.

The ring closure in scheme c) is carried out by reacting the diamine with phosgene, or a urea derivative (compounds wherein X is O), thiocarbonyl diimidazole (compounds wherein X is S), or bromcyan (compounds wherein X is $NH_2$) using conventional procedures. Compounds of formula (I) wherein X is N-alkyl or N-(alkyl)$_2$ can be prepared by alkylation of compounds of formula (I) wherein X is $NH_2$, with an alkylhalogenide or other suitable alkylating reagent.

Compounds of formula (I) wherein X is imino can be prepared by reacting a compound of formula (I) with ammonia.

Compounds of formula (I) wherein X is O-alkyl or S-alkyl is prepared from the compounds of formula (I) wherein X is O respectively S by standard alkylating procedures, e.g. by reaction with an appropriate alkylhalogenide or with an appropriate dialkylsulfate.

Compounds of formula (I) wherein $R^1$ is different from hydrogen is prepared from compounds of formula (I) wherein $R^1$ is hydrogen using conventional alkylation or acylation procedures.

Compounds of formula (I) wherein $R^3$ is alkyl is prepared from compounds of formula (I) wherein $R^3$ is hydrogen using conventional alkylation procedures.

Starting materials for the reactions in the schemes above are known compounds, or can be prepared by known procedures from commercially available materials.

The products of the reactions described herein are isolated in conventional manner such as extraction, crystallization, distillation, chromatography, and the like.

THE DRAWINGS

Figure 2:
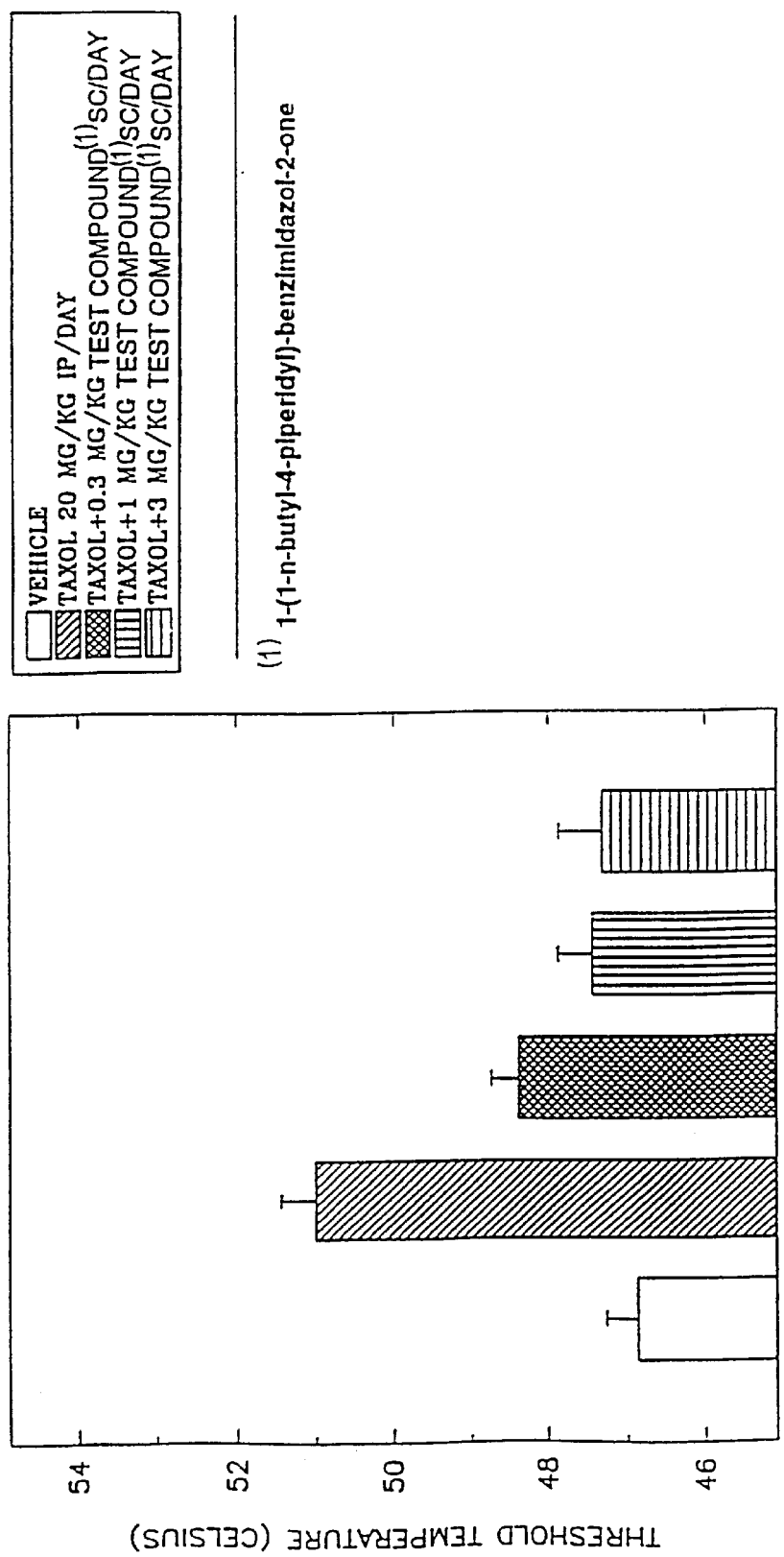
Figure 3:
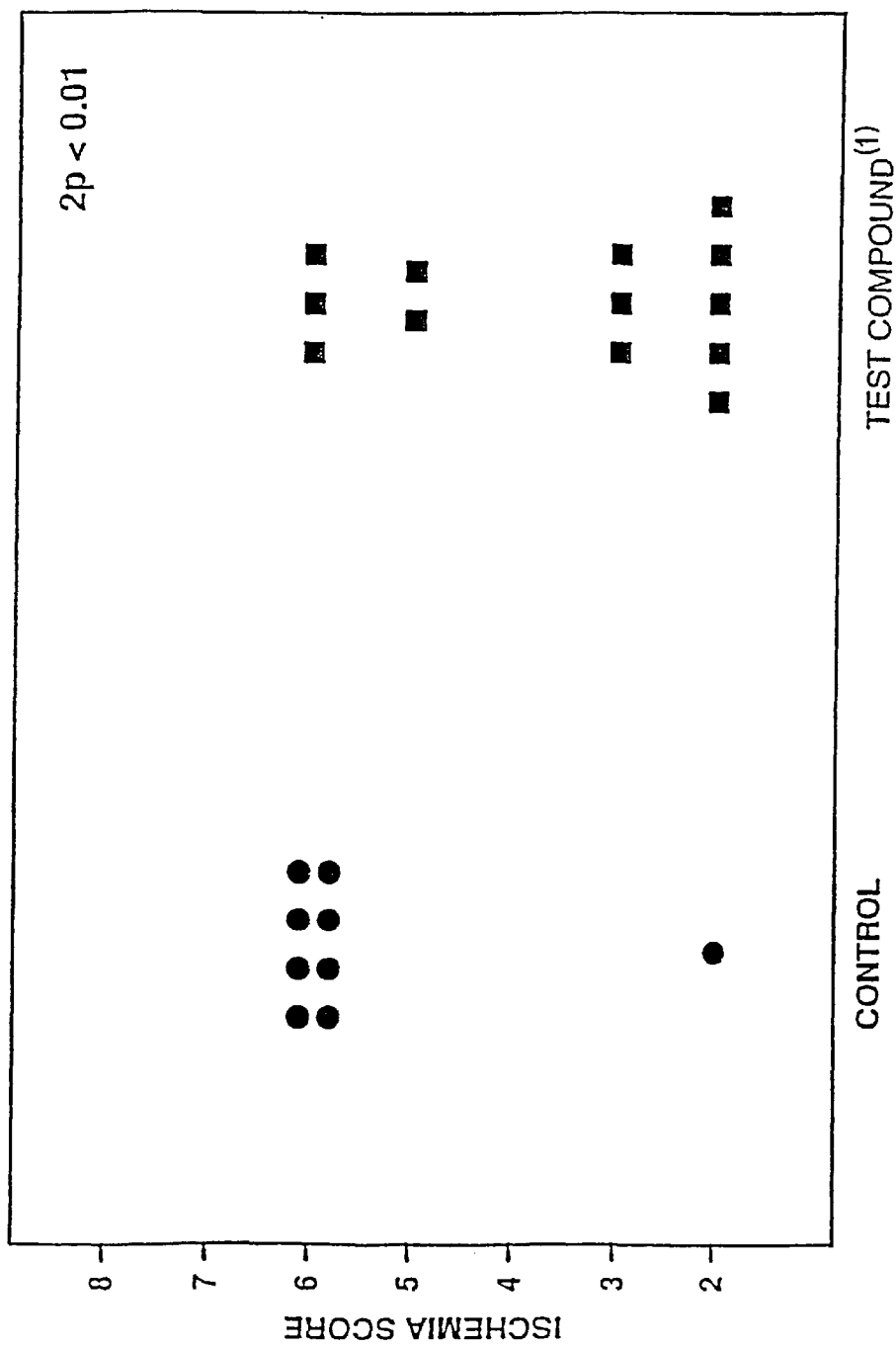

Reference is now made to the drawings for a better understanding of the invention, wherein:

FIG. 1 is a graph showing the improved survival rate of NGF-dependent DRG neurons, FIG. 2 is a graph showing prevention of the increase in tail flick treshold induced by taxol, and FIG. 3 is a graph showing neuroprotective effect in the gerbil 2-VO model.

BIOLOGICAL TESTING

The compound, 1-(1-n-butyl-4-piperidyl)-Benzimidazol-2-one has been tested for its ability to prevent inhibition of NGF induced neurite extention in PC12 cells by two cancer thereapeutics in the following test:

CHEMICALLY INDUCED NEURITE DEGENERATION IN PC12 CELLS

Neurite formation in PC12 cells may be strongly influenced by the presence of neurotoxins including the cancer therapeutics taxol and cisplatin.

PC12 cells ($2.5 \times 10^3/cm^2$) were incubated for 24 hours in medium supplemented with 10% fetal calf serum. Medium was exchanged to serum-free medium containing NGF (0, 1, 3, 5 or $10 \times 10^{-11}$ M), anti-cancer drugs (cisplatin or taxol: 0, $1 \times 10^{-8}$ M to $1 \times 10^{-5}$ M), and 1-(1-n-butyl-4-piperidyl)-benzimidazol-2-one (0 or $1 \times 10^{-6}$ M). After incubation for 3 days the degree of neurite extension of PC12 cells was scored with a phase-contrast microscope according to the following criterions:

score 0; mean neurite length (M.N.L). $< \frac{1}{2} \times$ diameter of cell body (C.B.D.)

0.5; $\frac{1}{2} \times C.B.D. \leq M.N.L. < 1 \times C.B.D.$

1; $1 \times C.B.D. \leq M.N.L. < 2 \times C.B.D.$

2; $2 \times C.B.D. \leq M.N.L. < 3 \times C.B.D.$

3; $3 \times C.B.D. \leq M.N.L. < 4 \times C.B.D.$

4; $4 \times C.B.D. \leq M.N.L.$

The score obtained in the experiments is presented in the following Tables 1 and 2:

TABLE 1

Inhibitory effect of cisplatin on NGF-induced neurite extension in PC12 cells and preventive effect of the test compound on the inhibition by cisplatin (means of 3 experiments).

| cisplatin (M) | 1-(1-n-butyl-4-piperidyl)-benzimidazol-2-one $10^{-6}$M | NGF [$\times 10^{-11}$M] | | | |
|---|---|---|---|---|---|
| | | 0 | 3 | 5 | 10 |
| – | – | 0 | 1.7 | 3.0 | 4.0 |
| | + | 0 | 1.7 | 3.0 | 4.0 |
| $1.0 \times 10^{-8}$ | – | 0 | 1.3 | 3.0 | 3.7 |
| | + | 0 | 1.7 | 3.0 | 4.0 |
| $3.0 \times 10^{-8}$ | – | 0 | 1.0 | 1.7 | 3.0 |
| | + | 0 | 1.3 | 2.3 | 3.3 |
| $1.0 \times 10^{-7}$ | – | 0 | 0.8 | 1.3 | 2.3 |
| | + | 0 | 1.7 | 1.7 | 2.7 |
| $3.0 \times 10^{-7}$ | – | 0 | 0.5 | 1.0 | 2.0 |
| | + | 0 | 1.0 | 1.7 | 2.0 |
| $1.0 \times 10^{-6}$ | – | 0 | 0.5 | 1.0 | 1.3 |
| | + | 0 | 0.8 | 1.7 | 2.0 |
| $3.0 \times 10^{-6}$ | – | 0 | 0.5 | 1.0 | 1.3 |
| | + | 0 | 0.5 | 1.0 | 1.7 |
| $1.0 \times 10^{-5}$ | – | 0 | 0.0 | 0.3 | 0.5 |
| | + | 0 | 0.2 | 0.5 | 1.7 |

TABLE 2

Inhibitory effect of taxol on NGF-induced neurite extension in PC12 cell and preventive effect of the test compound on the inhibition by taxol.

| taxol (M) | 1-(1-n-butyl-4-piperidyl)-benzimidazol-2-one $10^{-6}$M | NGF [$\times 10^{-11}$M] | | | |
|---|---|---|---|---|---|
| | | 0 | 3 | 5 | 10 |
| – | – | 0 | 2.0 | 3.0 | 4.0 |
| | + | 0 | 2.0 | 3.0 | 3.7 |
| $1.0 \times 10^{-8}$ | – | 0 | 1.3 | 1.7 | 4.0 |
| | + | 0 | 2.0 | 2.0 | 3.7 |
| $3.0 \times 10^{-8}$ | – | 0 | 0.7 | 1.0 | 2.7 |
| | + | 0 | 1.7 | 1.7 | 3.0 |
| $1.0 \times 10^{-7}$ | – | 0 | 0.7 | 0.8 | 1.7 |
| | + | 0 | 1.0 | 0.8 | 2.0 |
| $3.0 \times 10^{-7}$ | – | 0 | 0 | 0.5 | 0.5 |
| | + | 0 | 0.2 | 0.8 | 1.0 |
| $1.0 \times 10^{-6}$ | – | 0 | 0 | 0 | 0.2 |
| | + | 0 | 0 | 0.3 | 0.3 |
| $3.0 \times 10^{-6}$ | – | 0 | 0 | 0 | 0.2 |
| | + | 0 | 0 | 0.5 | 0.2 |
| $1.0 \times 10^{-5}$ | – | 0 | 0 | 0 | 0 |
| | + | 0 | 0 | 0 | 0 |

It is concluded that both taxol and cisplatin showed a concentration-dependent inhibition of NGF-induced neurite extension. The test compound, 1-(1-n-butyl-4-piperidyl)-benzimidazol-2-one showed a rightward shift of the dose-inhibition curves for both anti-cancer drugs.

The compound, 1-(1-n-butyl-4-piperidyl)-benzimidazol-2-one has also been tested for its effect on the survival of rat P2 DRG neurons using the following test:

NGF DEPENDENT SURVIVAL OF DRG NEURONS

Method: DRGs were dissected from P2 rat pups, enzymatically dissociated and the cell suspension seeded in serum free medium with or without NGF or test compound onto poly-L-lysin/laminin coated 4.5 mm 96 well A/Z culture plates (1000 cells per well).

After 20 hours in culture 3-(4,5-dimethylthiazol-2-yl)-2,5-diphenyltetrazolium bromide (MTT), 0.15 mg/ml final concentration, was added and the incubation continued for further 4 hours. The incubation was terminated by addition of acidic isopropanol and the dissolved blue formazan formed from MTT in the live cells were measured spectrophotometrically at 570 nm.

The results obtained are shown in FIG. 1.

In conclusion, addition of the test compound, 1-(1-n-butyl-4-piperidyl)-benzimidazol-2-one at 0.3 µM gave a significantly higher survival rate in 24 h cultures of rat P2 DRG neurons.

The compound, 1-(1-n-butyl-4-piperidyl)-benzimidazol-2-one has also been tested for its ability to prevent taxol induced peripheral neuropathy using the following test:

TAXOL-INDUCED LOSS OF PAIN SENSATION

Introduction: Taxol is an anticancer drug against solid tumors but the development of peripheral neuropathy has been dose limiting (Wiernik et al. 1987, Lipton et al. 1989). Taxol has also been shown to induce peripheral neuropathy in mice, and the effect can be inhibited by Nerve Growth Factor (NGF) (Apfel et al. 1991). We have tested whether the test compound could prevent taxol-induced peripheral neuropathy in mice with a paradigm similar to Apfel's experiments.

Method: In all experiments female NMRI mice (Bomholtgaard Breeding Center) habituated to the laboratory for at least 16 hours and with tap water and altromin food ad libitum were used. After taxol administration the tail flick threshold was evaluated the following way:

Female NMRI mice were separated into 5 groups (n=15) and administered 10% Tween 80 (0.3 ml i.p.), 20 mg/kg taxol i.p. or 20 mg/kg taxol plus 0.3, 1 or 3 mg/kg test compound s.c. daily for 6 consecutive days. In order to protect the animals from the consequences of insufficient nourishment all groups were administered 1 ml Babymin$^A$ p.o. daily. Babymin$^A$ is a breast milk substitute consisting of water, milk, electrolytes and vitamins. Test compound and Babymin$^A$ were also administered on the day after the discontinuation of taxol treatment.

The taxol treatment decreased the food and water intake in a reversible manner. Even though the animals were administered 1 ml Babymin$^A$ daily they lost in body weight (results not shown) but only to a limited extent and the mice were generally in a good condition and survived throughout the experiment.

Two days after the discontinuation of taxol treatment the tail flick threshold was measured: The mice were, one at a time, gently restrained in a 50 ml syringe with the tail exposed. The tail was submerged into hot water at 45, 47, 49, 51, 53 and 55° C. for 5 sec and the lowest temperature inducing a tail flick response was noted for each mouse. (If a mouse flicked at e.g. 49° C., it was not tested at higher temperatures).

The results, obtained and presented in FIG. 2, show that 1-(1-n-butyl-4-piperidyl)-benzimidazol-2-one at 0.3, 1, and 3 mg/kg very efficiently prevents the increase in tail flick threshold induced by taxol.

The compound, 1-(1-n-butyl-4-piperidyl)-benzimidazol-2-one has also been tested for its neuroprotective effect in the following animal ischemia model:

TRANSIENT FOREBRAIN ISCHEMIA MODEL (2-VO GERBILS)

Gerbils were anaesthetized with halothane, right and left carotid arteries located and occluded for 4 minutes. Animals were kept warm before and after the operation using heating lamps. During the operation the gerbils were placed on heating plates, body temperature controlled and maintained at 37±0.5° C. Four days later, the animals were sacrificed, brains removed and cooled to −70° C. Thereafter, the brains were sectioned in 20 mm thick sections of which 5–7 with hippocampal tissue were selected and stained with hematoxylin eosine (HE).

Based upon the degree of hippocampal damage, each hippocampus was categorised into one of four groups (Group 1: no damage in the CA1-layer; Group 2: the CA1-layer partly damaged; Group 3: the CA1-layer completely damaged; and Group 4: damage in more than just the CA1-layer). The total ischemic score was obtained as the sum of the right and left scores. The test results are presented in FIG. 3.

1-(1-n-butyl-4-piperidyl)-benzimidazol-2-one showed significant neuroprotective effect in the gerbil 2-VO model, when dosed at 30 mg/kg s.c. 15 minutes post-occlusion and once a day for the following two days.

The pharmacological activities, characteristics, and properties of the compounds of the present invention, as evidenced by the foregoing test data and results, is predictive of utility of the compounds of the invention in the treatment of the physiological conditions, ailments, disorders, and diseases enumerated herein, including the treatment of peripheral neuropathy, traumatic lesions of peripheral nerves, the medulla, and/or the spinal cord, and cerebral ischaemic neuronal damage.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, one (1) to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms-may comprise, as the active component, either a compound of the invention or a phaarmaceutically acceptable salt of a compound of the invention.

For preparing pharmaceutical compositions from the compounds of the present invention, phaarmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted into the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated into solutions in aqueous polyethylene glycol.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

METHOD OF TREATING

Due to the high degree of activity, the compounds of formula (I) may be administered to a subject, e.g., a living animal body, in need of alleviation, treatment, or amelioration of a disorder which is responsive to the activity or influence of neurotrophic agents, including responsive to nerve growth factor activation or potentiation, and/or protein kinase C activation or potentiation and/or tyrosine kinase(s) activation or potentiation. Such disorders or diseases include traumatic lesions of peripheral nerves,the medulla, and/or the spinal cord, cerebral ischaemic neuronal damage, neuropathy and especially peripheral neuropathy, memory impairment connected to dementia, Alzheimer's disease, Parkinson's disease, amyotrophic lateral sclerosis, or any other neurodegenerative disease. The compounds of the invention are preferably administered in the form of an acid addition salt thereof, concurrently, simultaneously, or together with a pharmaceutically acceptable carrier or diluent, especially and preferably in the form of a pharmaceutical composition thereof, whether by the oral, rectal, or parenteral (including subcutaneous) route, in an effective amount. Suitable dosage ranges are 1–500 milligrams daily, preferably 1–100 milligrams daily, and especially 1–30 milligrams daily, depending as usual upon the exact mode of administration, form in which administered, the indication toward which the administration is directed, the subject involved and the body weight of the subject involved, and the preferences and experience of the physician or veterinarian in charge.

The following examples will illustrate the invention further; however they are not to be construed as limiting.

EXAMPLE 1

1-(1-Butyl-piperidin-4-yl)-1,3-dihydro-benzimidazol-2-one oxalate and 1-Butyl-3-(1-butyl-piperidin-4-yl)-1,3-dihydro-benzimidazol-2-one oxalate.

A mixture of 1-piperidin-4-yl-1,3-dihydro-benzimidazol-2-one (1.96 g, 9 mmol), 1-butylbromide (1.46 ml, 13.5 mmol) and potassium carbonate (1.86 g, 13.5 mmol) in ethanol (20 ml) was refluxed for 18 hours. After cooling to ambient temperature acetone (5 ml) and diethyl ether (5 ml) was added to the reaction mixture, followed by filtration and evaporation of the filtrate in vacuo. The crude product was subjected to column chromatography using a mixture of chloroform and methanol (7/1) containing 1% concentrated ammonium hydroxide as eluent and 1-butyl-3-(1-butyl-piperidin-4-yl)-1,3-dihydro-benzimidazol-2-one was eluted first followed by 1-(1-butyl-piperidin-4-yl)-1,3-dihydro-benzimidazol-2-one contaminated with the di-butylated product. The last product was recrystallized from ethanol and 1-(1-butyl-piperidin-4-yl)-1,3-dihydro-benzimidazol-2-one was isolated as a white crystalline compound, which was dissolved in a small amount of methylene chloride whereafter oxalic acid was added. The formed 1-(1-butyl-piperidin-4-yl)-1,3-dihydro-benzimidazol-2-one oxalate was collected by filtration, white crystals, m.p. 209–214° C. 1-butyl-3-(1-butyl-piperidin-4-yl)-1,3-dihydro-benzimidazol-2-one as an oil was dissolved in a small amount of methylene chloride and oxalic acid was added. Only a yellow syrup of this product was obtained.

In exactly the same manner the following compounds were prepared:

1-(1-hexyl-piperidin-4-yl)-1,3-dihydro-benzimidazol-2-one oxalate, M.p. 207–209° C.

1-(1-octyl-piperidin-4-yl)-1,3-dihydo-benzimidazol-2-one oxalate, M.p. 121–123° C.

1-(1-benzyl-piperidin-4-yl)-1,3-dihydro-benzimidazol-2-one oxalate, M.p. 225–227° C.

1-(1-ethyl-piperidin-4-yl)-1,3-dihydro-benzimidazol-2-one oxalate, M.p. 196–199° C.

EXAMPLE 2 a) 1-Benzyl-4-(4-fluoro-2-nitrophenyl-amino)-piperidine.

A mixture of 2,5-difluoro-nitrobenzene (5.29 g, 33.3 mmol), 4-amino-1-benzylpiperidine (6.33 g, 33.3 mmol) and potassium carbonate (5.06 g, 36.6 mmol) in absolute N,N-dimethyl formamide was stirred at room temperature for 23 hours. Water (100 ml) was added and the mixture was extracted twice with ethyl acetate (50 ml). After drying and concentration in vacuo of the combined organic phases, the crude product was subjected to flash chromatography using methylene chloride containing 4% ethanol as eluent yielding the title compound as orange crystals, m.p. 86–880 C.

b) 1-Benzyl-4-(2-amino-4-fluorophenyl-amino)-piperidine.

To a solution of 1-benzyl-4-(4-fluoro-2-nitrophenyl-amino)-piperidine (6.55 g, 20 mmol) in tetrahydrofuran (70 ml) was added palladium on activated carbon (5%, 0.65 g) and the mixture was hydrogenated at atmospheric pressure. The reaction mixture was filtered through celite into a solution of hydrochloric acid in methanol (1.8 M, 22 ml) and the mixture was concentrated in vacuo yielding the title compound as crystals, m.p. 118–122° C.

c) 1-(1-Benzyl-piperidin-4-yl)-5-fluoro-2-aminobenzimidazole.

A solution of 1-benzyl-4-(2-amino-4-fluorophenyl-amino)-piperidine (7.41 g, 20 mmol), triethyl amine (2.8 ml, 20 mmol) and bromocyan (2.75 g, 26 mmol) was stirred at room temperature for seven days and the mixture was poured into water (200 ml). The aqueous phase was washed with diethyl ether (3 times 70 ml) and the pH was adjusted to ten by addition of a 2 M sodium hydroxide solution followed by extraction with diethyl ether (2 times 100 ml) and concentration in vacuo. The crude product was dissolved in ethanol, refluxed with activated charcoal, filtered through celite and concentrated in vacuo. Column chromatography using methylene chloride containing 4% ethanol as eluent yielded the title compound as a glass, m.p. 71–80° C.

EXAMPLE 3

6-Bromo-1-(1-butyl-piperidin-4-yl)-1,3-dihydro-benzimidazol-2-one.

1-(1-butyl-piperidin-4-yl)-1,3-dihydro-benzimidazol-2-one (0.5 g, 1.38 mmol) was suspended in acetic acid (5 ml) and added bromine (0.07 ml, 1.38 ml) in acetic acid (1 ml). The reaction mixture was stirred at room temperature for 90 minutes, then added water (5 ml) and filtrated, the residue was washed with water, then added ethyl acetate (10 ml) and 1 M sodium hydroxide (aq.) (10 ml). The organic phase was dried with magnesium sulphate and evaporated to dryness. The residue was chromatographed on kieselgel 60 and eluted with ethyl acetate/methanol (7/3 (v/v)). The product fractions was evaporated to a foam. Yield 40 mg (0.1 mmol, 8%). M.p. 179–181° C.

EXAMPLE 4

1-(1-Acetyl-piperidin-4-yl)-1,3-dihydro-benzimidazol-2-one 1-piperidin-4-yl-1,3-dihydro-benzimidazol-2-one (0.2 g, 0.9 mmol) and acetic anhydride (0.2 ml, 2 mmol) was dissolved in acetic acid (5 ml) and stirred at room temperature for 30 minutes, then added water (10 ml) and evaporated to and oil. This was crystallized from ethanol (96%). Yield 0.18 g (0.7 mmol, 77 %). M.p. 212–214° C.

EXAMPLE 5

1-(1-Phenethyl-piperidin-4-yl)-1,3-dihydro-benzimidazol-2-one.

A mixture of 1-piperidin-4-yl-1,3-dihydro-benzimidazol-2-one (0.5 g, 2.3 mmol), 2-phenyl-ethylbromid (0.34 ml, 2.5 mmol), triethylamine (0.35 ml, 2.5 mmol) and sodium iodide (0.01 g, 0.67 mmol) in dry N,N-dimethyl formamide (5 ml) was stirred at 100° C. for 3 hours. The reaction mixture was cooled to room temperature, and then poured into water (20 ml). The product precipitated upon stirring on a ice/water bath and was isolated by filtration. Yield 0.45 g (1.4 mmol, 61%). M.p. 181–185° C.

In the exactly the same manner was the following compounds prepared:

1-(1-Cyclopropylmethyl-piperidin-4-yl)-1,3-dihydro-benzimidazol-2-one. M.p. 168–170° C.

1-[1-(2,2-Diethoxy-ethyl)-piperidin-4-yl]-1,3-dihydro-benzimidazol-2-one. M.p. 106–110° C.

1-[1-(2-oxo-2-phenyl-ethyl)-piperidin-4-yl]-1,3-dihydro-benzimidazol-2-one. M.p. 164–167° C.

1-[1-(2-Methoxy-ethyl)piperidin-4-yl]-1,3-dihydro-benzimidazol-2-one. M.p. 95–98° C.

1-[1-(4-tert-Butyl-benzyl)-piperidin-4-yl]-1,3-dihydro-benzimidazol-2-one. M.p. 85–89° C.

1-[1-(3-Methyl-but-2-enyl)-piperidin-4-yl]-1,3-dihydro-bnezimidazol-2-one. M.p.75–80° C.

What is claimed is:

1. A compound having the formula:

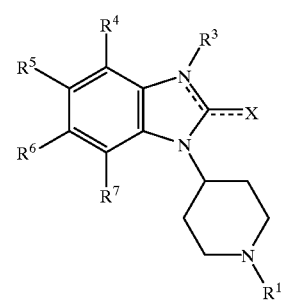

(I)

wherein $R^3$ is a non-existing, hydrogen, or alkyl, and the dotted bonds are optional bonds allowing tautomeric isomers compatible with X and $R^3$;

X is O;

$R^1$ is ethyl, propyl, isopropyl, butyl, isobutyl, tert-butyl, pentyl, hexyl, $C_{2-10}$-alkenyl, $C_{2-10}$-alkynyl, $C_{3-7}$-cycloalkyl, $C_{3-7}$-cycloalkyl-$C_{1-10}$-alkyl, $C_{1-10}$-alkoxy-$C_{1-10}$-alkyl, or di-$C_{1-10}$-alkoxy-$C_{1-10}$-alkyl; and $R^4$, $R^5$, $R^6$ and $R^7$ independently of each other are hydrogen; halogen; amino; nitro; CN; $CF_3$; COOH; COO—$C_{1-10}$-alkyl; $C_{1-10}$-alkyl; acyl; $C_{1-10}$-alkoxy; —$(CH_2)_n$—OH wherein n is 0, 1, 2, or 3; —$(CH2)_m$—O-alkyl wherein m is 0, 1, 2, or 3; —$(CH_2)_p$-O-acyl wherein p is 0, 1, 2, or 3; or a pharmaceutically acceptable addition salt thereof.

2. A compound of claim 1 which is 1-(1-n-butyl-4-piperidyl)-benzimidazol-2-one;

1-(1-butyl-4-piperidin-4-yl)-1,3-dihydro-benzimidazol-2-one;

1-butyl-3-(1-butyl-4-piperidin 4-yl)-1,3-dihydro-benzimidazol-2-one;

1-(1-hexyl-piperidin-4-yl)-1,3-dihydro-benzimidazol-2-one;

1-(1-octyl-piperidin-4-yl)-1,3-dihydro-benzimidazol-2-one;

1-(1-ethyl-piperidin-4-yl)-1,3-dihydro-benzimidazol-2-one;

6-bromo-1-(1-butyl-4-piperidin-4-yl)-1,3-dihydro-benzimidazol-2-one;

1-(1-phenylethyl-piperidin-4-yl)-1,3-dihydro-benzimidazol-2-one;

1-(1-cyclopropylmethyl-piperidin-4-yl)-1,3-dihydro-benzimidazol-2-one;

1-[1-(2,2-diethoxy-ethyl)-piperidin-4-yl]-1,3-dihydro-benzimidazol-2-one;

1-[1-(2-methoxy-ethyl)-piperidin-4-yl]-1,3-dihydro-benzimidazol-2-one;

1-[1-(4-tert-butyl-benzyl)-piperidin-4-yl]-1,3-dihydro-benzimidazol-2-one; or

1-[1-(3-methyl-but-2-enyl)-piperidin-4-yl]-1,3-dihydro-benzimidazol-2-one; or a pharmaceutically acceptable addition salt thereof.

3. A pharmaceutical composition comprising a therapeutically effective amount of a compound of claim 1, or a pharmaceutically acceptable addition salt thereof, together with at least one pharmaceutically acceptable carrier or diluent.

4. A method of treating or preventing a neurodegenerative disease of a patient or animal in need thereof which comprises administering to said patient or animal a therapeutically effective amount of a compound selected from those having the formula:

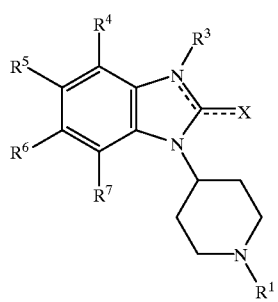

(I)

wherein $R^3$ is a non-existing, hydrogen, or alkyl, and the dotted bonds are optional bonds allowing tautomeric isomers compatible with X and $R^3$;

X is O;

$R^1$ is ethyl, propyl, isopropyl, butyl, isobutyl, tert-butyl, pentyl, hexyl, $C_{2-10}$-alkenyl, $C_{2-10}$-alkynyl, $C_{3-7}$-cycloalkyl, $C_{3-7}$-cycloalkyl-$C_{1-10}$-alkyl, $C_{1-10}$-alkoxy-$C_{1-10}$alkyl, or di-$C_{1-10}$alkoxy-$C_{1-10}$alkyl; and $R^4$, $R^5$, $R^6$ and $R^7$ independenty of each other are hydrogen; halogen; amino; nitro; CN; $CF_3$; COOH; COO-$C_{1-10}$-alkyl; $C_{1-10}$-alkyl; acyl; $C_{1-10}$-alkoxy, —$(CH_2)_n$—OH wherein n is 0, 1, 2, or 3; —$(CH_2)_m$—O-alyl wherein m is 0, 1, 2, or 3; —$(CH_2)_p$—O-acyl wherein p is 0, 1, 2, or 3; or a phannaceutically acceptable addition salt thereof.

5. The method of claim 4, wherein the neurodegenerative disease is dementia, Alzheimer's disease, Parkinson's disease, Huntington's disease, or amyotrophic lateral sclerosis.

6. The method according to claim 4, wherein the neurodegenerative disease is cerebral ischaeric neuronal damage, central neuropathy, peripheral neuropathy, Alzheimer's disease, Huntington's disease, Parkinson's disease or amyotrophic lateral sclerosis.

7. A method of claim 4, wherein the compound employed is 1-(1-n-butyl-4-piperidyl)-benzimidazol-2-one;

1-(1-butyl-4-piperidin-4-yl)-1,3-dihydro-benzimidazol-2-one;

1-butyl-3-(1-butyl-4-piperidin 4-yl)-1,3-dihydro-benzimidazol-2-one;

1-(1-hexyl-piperidin-4-yl) -1,3-dihydro-benzimidazol-2-one;

1-(1-octyl-piperidin-4-yl)-1,3-dihydro-benzimidazol-2-one;

1-(1-ethyl-piperidin-4-yl)-1,3-dihydro-benzimidazol-2-one;

6-bromo-1-(1-butyl-4-piperidin-4-yl)-1,3-dihydro-benzimidazol-2-one;

1-(1-phenylethyl-piperidin-4-yl)-1,3-dihydro-benzimidazol-2-one;

—(1-cyclopropylmethyl-piperidin-4-yl)-1,3-dihydro-benzimidazol-2-one;

—[1-(2,2-diethoxy-ethyl)-piperidin-4-yl]-1,3-dihydro-benzimidazol-2-one;

—[1-(2-methoxy-ethyl)-piperidin-4-yl]-1,3-dihydro-benzimidazol-2-one;

1-[1-(4-tert-butyl-benzyl) -piperidin-4-yl]-1,3-dihydro-benzimidazol-2-one; or

1-[1-(3-methyl-but-2-enyl)-piperidin-4-yl]-1,3-dihydro-benzimidazol-2-one; or a pharmaceutically acceptable addition salt thereof.

8. A method of promoting peripheral or central neuronal growth in a patient or aniinal in need thereof, which comprises administering said patient or animna a therapeutically effective amo-ant of a compound selected from those having the formula:

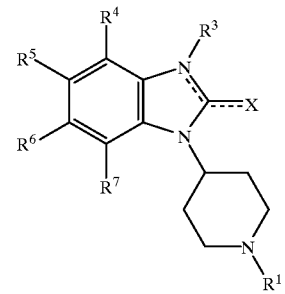

(I)

wherein $R^3$ is a non-existing, hydrogen, or alkyl, and the dotted bonds are optional bonds allowing tautomeric isomers compatible with X and $R^3$;

X is O;

$R^1$ is ethyl, propyl, isopropyl, butyl, isobutyl, tert-butyl, pentyl, hexyl, $C_{2-10}$-alkenyl, $C_{2-10}$-alkynyl, $C_{3-7}$-cycloalkyl, $C_{3-7}$-cycloalkyl-$C_{1-10}$-alkyl, $C_{1-10}$-alkoxy-$C_{1-10}$-alkyl, or di-$C_{1-10}$-alkoxy-$C_{1-10}$-alkyk; and $R^4$, $R^5$, $R^6$ and $R^7$ independently of each other are hydrogen; halogen; amrnino; nitro; CN; $CF_3$; COOH; COO-$C_{1-10}$alkyl; $C_{1-10}$-alkyl; acyl; $C_{1-10}$-alkoxy; —$(CH_2)_n$—OH wherein n is 0, 1, 2, or 3; —$(CH_2)_m$—O-alkyl wherein m is 0, 1., 2, or 3; —$(CH_2)_p$—O-acyl wherein p is 0, 1, 2, or 3; or a pharmaceutically acceptable addition salt thereof.

9. The method according to claim 8, wherein said patient or animal in need thereof has a traumatic lesion of peripheral nerves, the medulla and/or the spinal cord, cerebral ischaemic neuronal damage, central neuropathy and peripheral neuropathy.

10. A method of claim 8, wherein the compound employed is 1-(1-n-butyl-4-piperidyl)-benzimidazol-2-one;

1-(1-butyl-4-piperidin-4-yl)-1,3-dihydro-benzidazol-2-one;

1-butyl-3-(1-butyl-4-piperidin-4-yl)-1,3-dihydro-benzimidazol-2-one;

1-(1-hexyl-piperidin-4-yl)-1,3-dihydro-benzirrnidazol-2-one;

1-(1-octyl-piperidin-4-yl)-1,3-dihydro-benzimidazol-2-one;

1-(1-ethyl-piperidin-4-yl)-1,3-dihydro-benimidazol-2-one;

6-bromo-1-(1-butyl-4-piperidin-4-yl)-1,3-dihydro-benzimidazol-2-one;

1-(1-phenylethyl-piperidin-4-yl)-1,3-dihydro-benzimidazol-2-one;

—(1-cyclopropylmethyl-piperidin-4-yl)-1,3-dihydro-benzimdazol-2-one;

—[1-(2,2-diethoxy-ethyl)-piperidin-4-yl]-1, 3-dihydro-benzimidazol-2-one;

—[1-(2-methoy-ethyl)-piperidin-4-yl]-1, 3-dihydro-benzimnidazol-2-one;

1-[1-(4-tert-butyl-benzy)-pipeiidin-4-yl]-1,3-dihydro-beiidazol-2-one; or

1-[1-(3-methyl-but-2-enyl)-piperidin-4-yl]-1,3-dihydro-benzirnidazol-2-one; or a pharmaceutically acceptable addition salt thereof.

* * * * *